United States Patent
Shukla et al.

(10) Patent No.: US 11,273,124 B2
(45) Date of Patent: Mar. 15, 2022

(54) ANTIFUNGAL NANOPARTICLES FOR TARGETED TREATMENT OF FUNGAL INFECTIONS

(71) Applicant: BROWN UNIVERSITY, Providence, RI (US)

(72) Inventors: Anita Shukla, Providence, RI (US); Sarah Cowles, Bedford, MA (US); Noel Vera-Gonzalez, San Juan, PR (US); Christina Bailey-Hytholt, Millbury, MA (US); Eli Silvert, Woodbridge, CT (US)

(73) Assignee: Brown University, Providence, RI (US)

(*) Notice: Subject to any disclaimer, the term of this patent is extended or adjusted under 35 U.S.C. 154(b) by 0 days.

(21) Appl. No.: 16/828,761

(22) Filed: Mar. 24, 2020

(65) Prior Publication Data
US 2020/0368160 A1    Nov. 26, 2020

Related U.S. Application Data

(60) Provisional application No. 62/852,095, filed on May 23, 2019.

(51) Int. Cl.
| | |
|---|---|
| *A61K 9/127* | (2006.01) |
| *A61K 38/12* | (2006.01) |
| *A61P 31/10* | (2006.01) |
| *A61K 47/14* | (2017.01) |
| *A61K 47/42* | (2017.01) |

(52) U.S. Cl.
CPC .............. *A61K 9/127* (2013.01); *A61K 38/12* (2013.01); *A61K 47/14* (2013.01); *A61K 47/42* (2013.01); *A61P 31/10* (2018.01)

(58) Field of Classification Search
CPC ...................................................... A61K 9/127
See application file for complete search history.

(56) References Cited

U.S. PATENT DOCUMENTS

| | | | |
|---|---|---|---|
| 5,965,156 A | 10/1999 | Proffitt et al. | |
| 9,539,273 B2 | 1/2017 | Meehan et al. | |
| 2009/0238867 A1* | 9/2009 | Jenkins | A61K 38/12 424/455 |

(Continued)

FOREIGN PATENT DOCUMENTS

| | | |
|---|---|---|
| AU | 20057355 A | 1/2001 |
| EP | 3058958 B1 | 9/2018 |

(Continued)

OTHER PUBLICATIONS

Antonio P. Costa & Xiaoming Xu & Diane J. Burgess. "Freeze-Anneal-Thaw Cycling of Unilamellar Liposomes: Effect on Encapsulation Efficiency." Pharmaceutical Research, vol. 31, 2014, pp. 97-103. (Year: 2014).*

(Continued)

*Primary Examiner* — Isaac Shomer
(74) *Attorney, Agent, or Firm* — Adler Pollock & Sheehan P.C.

(57) ABSTRACT

The invention provides functionalized antifungal-loaded liposomal formulations targeting *Candida*, which minimize damage to healthy human cells, limit antimicrobial exposure, and reduce the development of antifungal resistance.

2 Claims, 7 Drawing Sheets
(7 of 7 Drawing Sheet(s) Filed in Color)
Specification includes a Sequence Listing.

(56) References Cited

U.S. PATENT DOCUMENTS

| | | | |
|---|---|---|---|
| 2013/0003061 A1* | 1/2013 | Amin | G01N 21/51 356/340 |
| 2014/0199241 A1* | 7/2014 | Yedgar | A61K 9/127 424/9.1 |
| 2016/0058864 A1* | 3/2016 | Meehan | A61K 47/545 424/450 |
| 2016/0199351 A1* | 7/2016 | Rappleye | A61K 31/4196 424/450 |
| 2017/0189392 A1* | 7/2017 | Tong | A61K 9/1278 |

FOREIGN PATENT DOCUMENTS

| | | | | |
|---|---|---|---|---|
| WO | 0100247 A9 | | 8/2002 | |
| WO | 2009005798 A2 | | 1/2009 | |
| WO | 2017037232 A1 | | 3/2017 | |
| WO | 2020146514 | † | 7/2020 | |
| WO | WO-2020146514 A1 | * | 7/2020 | A61K 47/6911 |

OTHER PUBLICATIONS

Seong-Cheol Park et al. "Targeting and synergistic action of an antifungal peptide in an antibiotic drug-delivery system." Journal of Controlled Release 256 (2017) 46-55. (Year: 2017).*

Rebecca A Drummond and Gordon D Brown. "The role of Dectin-1 in the host defence against fungal infections." Current Opinion in Microbiology, vol. 14, 2011, pp. 392-399. (Year: 2011).*

Woong Sik Jang, Xuewei Serene Li, Jianing N. Sun, and Mira Edgerton. "The P-113 Fragment of Histatin 5 Requires a Specific Peptide Sequence for Intracellular Translocation in Candida albicans, Which Is Independent of Cell Wall Binding." Antimicrobial Agents and Chemotherapy, 52(2), p. 497-504. (Year: 2008).*

David M. Rothstein, et al. "Anticandida Activity Is Retained in P-113, a 12-Amino-Acid Fragment of Histatin 5." Antimicrobial Agents and Chemotherapy, vol. 55 No. 5, May 2001, pp. 1367-1373. (Year: 2001).*

"Antibiotic Resistance Threats in the United States, 2013, U.S. Department Health & Human Services", Center for Disease Control and Prevention, 2013, 114 pages.

Barret,"From Natural Products to Clinically Useful Antifungals", Biochimica et Biophysica Acta, vol. 1587, 2002, pp. 224-233.

Brown et al., "Structure of the Fungal β-glucan-binding Immune Receptor Dectin-1: Implications for Function", Protein Science, vol. 16, 2007, pp. 1042-1052.

Grubb et al., "Candida albicans—Endothelial Cell Interactions: A Key Step in the Pathogenesis of Systemic Candidiasis", Infection and Immunity, vol. 76, No. 10, Oct. 2008, pp. 4370-4377.

Hamley, "Lipopeptides: From Self-assembly to Bioactivity", Chemical Communications—Royal Society of Chemistry, vol. 51, 2015, pp. 8574-8583.

Hashimoto et al., "Micafungin: A Sulfated Echinocandin", The Journal of Antibiotics, vol. 62, Issue 1, 2009, pp. 27-35.

Jang et al., "The P-113 Fragment of Histatin 5 Requires a Specific Peptide Sequence for Intracellular Translocation in Candida albicans, Which Is Independent of Cell Wall Binding" Antimicrobial Agents and Chemotherapy, vol. 52, No. 2, Feb. 2008, pp. 497-504.

Jiang et al., "Clearance of Intracellular Klebsiella Pneumoniae Infection Using Gentamicinloaded Nanoparticles", Journal of Controlled Release, vol. 279, 2018, pp. 316-325.

Kabir et al., "Candida albicans: A Model Organism for Studying Fungal Pathogens", International Scholarly Research Network, vol. 2012, Article ID 538694, 2012, pp. 1-15.

Li et al., "Using Galleria Mellonella—Candida Albicans Infection Model to Evaluate Antifungal Agents", Biological and Pharmaceutical Bulletin, vol. 36, Issue 9, 2013, pp. 1482-1487.

Moore et al., "AmBisome: Liposomal Formulation, Structure, Mechanism of Action and Pre-clinical Experience", Journal of Antimicrobial Chemotherapy, vol. 49, Suppl 1, Feb. 2002, pp. 21-30.

Odds et al., "Antifungal Agents: Mechanisms of Action", Trends Microbiology, vol. 11, Issue 6, Jun. 2003, pp. 272-279.

Perlin,"Echinocandin Resistance in Candida", Clinical Infectious Diseases, vol. 61, Suppl. 6, 2015, pp. S612-S617.

Pfaller et al., "Epidemiology of Invasive Candidiasis: A Persistent Public Health Problem", Clinical Microbiology Reviews, vol. 20, No. 1, Jan. 2007, pp. 133-163.

Richardson et al., "Special Issue: Mucosal Fungal Infections", Journal of Fungi, vol. 4, Issue 43, 2018, pp. 1-3.

Roemer et al., "Antifungal Drug Development: Challenges, Unmet Clinical Needs, and New Approaches", Cold Spring Harbor Perspectives in Medicine, vol. 4, Issue a019703, 2014, pp. 1-14.

Tsai et al., "Galleria Mellonella Infection Models for the Study of Bacterial Diseases and for Antimicrobial Drug Testing", Virulence, vol. 7, Issue 3, Apr. 2016, pp. 214-229.

Vallabhaneni et al., "Investigation of the First Seven Reported Cases of Candida Auris, A Globally Emerging Invasive, Multidrug-Resistant Fungus-Fungus", American Journal of Transplantation, vol. 17, 2017, pp. 296-299.

Vazquez et al., "Anidulafungin: A Novel Echinocandin", Reviews of Anti-infective Agents, Clinical Infectious Diseases, vol. 43, Issue 215, Jul. 15, 2006, pp. 215-222.

Walker et al., "The Viscoelastic Properties of the Fungal Cell Wall Allow Traffic of AmBisome as Intact Liposome Vesicles", American Society For Microbiology, vol. 9, Issue 1, Jan./Feb. 2018, pp. 1-15.

Rothstein et al., "Anticandida activity is retained in P-113, a 12-amino-acid fragment of histatin 5." Antimicrob. Agents Chemother. 45:1367-1373 (2001).

Ambati et al., "Dectin-1-targeted antifungal liposomes exhibit enhanced efficacy." mSphere, 4(1), e00025-19 (Jan./Feb. 2019).

\* cited by examiner
† cited by third party

ANTIFUNGAL NANOPARTICLES FOR TARGETED TREATMENT OF FUNGAL INFECTIONS

REFERENCE TO RELATED APPLICATIONS

This patent application claims priority to provisional patent application U.S. Ser. No. 62/852,095, filed May 23, 2019, entitled "Antifungal Nanoparticles for Targeted Treatment of Fungal Infections."

STATEMENT REGARDING FEDERALLY SPONSORED RESEARCH OR DEVELOPMENT

This invention was made with government support under grant no. N00014-17-1-2651 awarded by the Office of Naval Research and grant no. 1644760 awarded by the National Science Foundation. The government has certain rights in the invention.

FIELD OF THE INVENTION

This invention generally relates to a liposome with a therapeutic agent in it, and particularly to an antifungal therapeutic agent.

SEQUENCE LISTING

The instant application contains a Sequence Listing which has been submitted electronically in ASCII format and is hereby incorporated by reference in its entirety. Said ASCII copy, created on Feb. 5, 2021, is named 405505-575001US_SL.txt and is 809 bytes in size.

BACKGROUND OF THE INVENTION

Fungal infections are highly recurring and can require years to treat completely. Vallabhaneni et al., Am. J. Transplant., 17(1), 296-299 (2017). *Candida* spp. are the most common cause of these infections, leading to over 40,000 annual infections in the United States alone. "Antibiotic Resistance Threats in the United States." U.S. Dept. Health & Human Services, Center for Disease Control (2013). *Candida albicans* is an opportunistic pathogen that is the most common cause of fungal bloodstream infections. Kabir et al., ISRN Microbiol. 2012, 1-15 (2012). These infections can cause systemic candidiasis, an infection with a 33-54% mortality rate. Pfaller & Diekema, Clin. Microbiol. Rev., 20(1), 133-163 (2007). Systemic candidiasis has a high mortality rate of 33 to 54%, translating to over 10,000 deaths in the U.S. annually. Pfaller & Diekema, Clin. Microbiol. Rev., 20(1), 133-163 (2007). In the United States, annual treatment costs reach up to 4 billion dollars. Grubb et al., Infection & Immunity, 76(10), 4370-4377 (2008). Globally, these expenditures have now topped 15 billion USD. Richardson & Naglik, J. Fungi, 4(2), 43 (2018).

Antifungal resistance is a growing threat that increases the severity of fungal infections. Compounding these issues is the high toxicity and poor water solubility of many antifungals, limiting clinically viable therapeutic options. The antifungal drug repertoire is limited, with the last practical drug class (echinocandins) discovered back in 1974. Roemer & Krysan, Cold Spring Harbor Perspectives in Medicine, 4(5), a019703 (2014). Antifungal drug resistance is also a growing concern that further exacerbates the severity of fungal infections. Between 2004 and 2014, the number of echinocandin resistant *Candida albicans* strains doubled. Perlin, Clinical Infectious Diseases, 61(suppl. 6), S612-S617 (2015). Further complicating treatment, similarities between mammalian and fungal cells render most antifungals toxic to humans. The only current route of administration of the hydrophobic echinocandin is by a slow intravenous infusion.

Liposomes have been drug carriers because of their ability to increase circulation time, increased solubility, decrease off-site toxicity, penetrate biofilms, and localize to fungi. See, e.g., the liposome composition used in the commercial product, AmBisome®, liposomal amphotericin B, described in U.S. Pat. No. 5,965,156 (Proffit et al.) "Amphotericin B liposome preparation" and Adler-Moore & Proffitt, "AmBisome: Liposomal formulation, structure, mechanism of action and pre-clinical experience." Journal of Antimicrobial Chemotherapy, 49(1), 21-30 (2002). Currently, there are only a few commercial antifungal liposome formulations.

Because of the rise in antimicrobial drug resistance, there is a need in the medical art for targeted drug delivery formulations that limit unnecessary exposure to antimicrobials. There is a need for drug delivery systems that reduce antifungal resistance, off-site toxicity, and the number of treatment doses while increasing antifungal solubility, penetration through biofilms, and in vivo circulation times.

SUMMARY OF THE INVENTION

The invention provides an antifungal-encapsulating liposomal nanoparticle formulation that can address these needs. The invention provides functionalized antifungal-loaded liposomal formulations targeting *Candida*. The formulations minimize damage to healthy human cells, limit antimicrobial exposure, and reduce the development of antifungal resistance. See FIG. 1.

In the first embodiment, the invention provides a liposomal formulation comprising an antifungal. Among the antifungals that can be formulated into a liposomal formulation include the antifungal drug classes of azoles, polyenes, echinocandins, allylamines, and nucleosides. The specific antifungal therapeutics that can be formulated into a liposomal formulation include, but are not limited to, echinocandin B, cilofungin, micafungin, and caspofungin. In a second embodiment, the antifungal is an antifungal lipopeptide. In a third embodiment, the antifungal is an echinocandin. In a fourth embodiment, the antifungal is anidulafungin. The inventors have incorporated the antifungal lipopeptide anidulafungin into unilamellar liposomes.

In a fifth embodiment, the invention provides a functionalized liposomal composition comprising an antifungal and comprising P-113Q2.10 peptide (SEQ ID NO: 2) decoration as a targeting moiety (P-113Q2.10-PEG ("P-113Q2.10" disclosed as SEQ ID NO: 2)). The liposomes incorporate P-113Q2.10 (SEQ ID NO: 2). The invention provides decorated liposomes with poly(ethylene glycol) (PEG) by combining lipids (phosphoethanolamine) functionalized with PEG into the vesicle composition. The PEG, functionalized with dibenzocyclooctyne (DBCO), can then be covalently attached to azide-functionalized P-113Q2.10 (SEQ ID NO: 2) using strain promoted click chemistry. The fungal cell localization can be accomplished using PEG-P113Q2.10 ("P113Q2.10" disclosed as SEQ ID NO: 2) or palmitic acid-P113Q2.10 ("P113Q2.10" disclosed as SEQ ID NO: 2) functionalized liposomes. The result of this fungal cell localization can be tested using flow cytometry and confocal microscopy. The PEG functionalized with dibenzocyclooctyne (DBCO) can be covalently attached to azide-functionalized P-113Q2.10 (SEQ ID NO: 2) using strain promoted click chemistry. Liposomes containing PEG-DBCO have an average diameter of 10 to 1000 nm.

In a sixth embodiment, the invention provides a functionalized liposomal composition comprising an antifungal. Dectin-1, a transmembrane protein that binds to yeast cell wall glucan, can be a targeting moiety. The inventors incorporated dectin-1 by adding it to the re-hydrated lipid film formed before the freeze-thaw and extrusion process. Liposomes containing dectin-1 have an average diameter of 10 to 1000 nm. Transmission electron microscopy (TEM) of the dectin-1-containing vesicles also confirmed their size and morphology.

In a seventh embodiment, the invention provides a method of making a liposomal formulation comprising antifungal lipopeptides, azoles, polyenes, allylamines, or nucleosides comprising, but not limited to, a freeze-thaw step, a sonication step, and an extrusion step. The liposomal formulation includes, but is not limited to, the lipids hydrogenated soy phosphatidylcholine, cholesterol, phosphatidylglycerol, α-tocopherol, and anidulafungin. In an eighth embodiment, the invention provides a liposomal formulation made by the freeze-thaw, sonication and extrusion steps, wherein the liposomal formulation comprises the lipids, but not limited to, hydrogenated soy phosphatidylcholine, cholesterol, phosphatidylglycerol, α-tocopherol, and anidulafungin.

In a ninth embodiment, the invention provides a method of making a liposomal formulation comprising, but not limited to, a freeze-thaw step, a sonication step, and an extrusion step. The liposomal formulation includes the lipids, but is not limited to, hydrogenated soy phosphatidylcholine, cholesterol, phosphatidylglycerol, α-tocopherol, and anidulafungin at a mass concentration (% w/w) of, but not limited to, 60.73%, 14.83%, 23.95%, 0.18%, and 0.31% respectively. In a tenth embodiment, the method of making a liposomal formulation results in a liposomal formulation comprising the lipids, but not limited to, hydrogenated soy phosphatidylcholine, cholesterol, phosphatidylglycerol, α-tocopherol, and anidulafungin at a mass concentration (% w/w) of, but not limited to, 60.73%, 14.83%, 23.95%, 0.18%, and 0.31% respectively.

In an eleventh embodiment, the method of making a liposomal formulation results in liposomes with an average diameter of 10 to 1000 (polydispersity index (PDI)=0 to 0.5). In a twelfth embodiment, the method of making a liposomal formulation further comprises the steps of measuring vesicle size and PDI using dynamic light scattering (DLS) and transmission electron microscopy (TEM).

The 1× anidulafungin liposomes showed remarkable stability in solution at 4° C. for up to 140 days, with no significant changes in vesicle size. The liposomes were as effective as freshly prepared liposomes in inhibiting *Candida* growth.

In a thirteenth embodiment, the invention provides a method for treating *Candida* infections comprising the step of administering a functionalized and non-functionalized liposomal formulation comprising an antifungal, such as anidulafungin. In a fourteenth embodiment, the method for treating bloodstream *Candida* infections comprises the step of administering a liposomal formulation comprising an antifungal, such as anidulafungin. The administration can be by any medically-acceptable route, including intravenous, subcutaneous, intraperitoneal, and the like. In a fifteenth embodiment, the method for treating candidiasis is by administering a liposomal formulation comprising an antifungal lipopeptide, such as anidulafungin. In a sixteenth embodiment, the method for treating systemic candidiasis is by administering a liposomal formulation comprising an antifungal lipopeptide, such as anidulafungin. In a seventeenth embodiment, the method for treating *Candida* biofilms comprises the step of administering a liposomal formulation comprising an antifungal lipopeptide, such as anidulafungin.

In an eighteenth embodiment, the invention provides a method for treating *Candida* infections comprising the step of administering liposomes with a minimum inhibitory concentration range of these liposomes of 1.5 to 12.5 μg/mL.

In a nineteenth embodiment, the invention provides a method for treating *Candida* biofilms comprising the step of administering liposomes where the treatment reduces fungal burden by five-fold after only twenty-four hours.

Anidulafungin liposomes were more effective than free drug against *Candida* biofilms, which are significantly harder to treat than planktonic fungi. 1×, 5×, and 10× anidulafungin liposomes at 1.25 mg/mL were effective at disrupting pre-formed *Candida* biofilms. This result highlights the importance of liposomal carriers in increasing the efficacy of antifungals against biofilms.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Industrial Applicability

Figure 1:
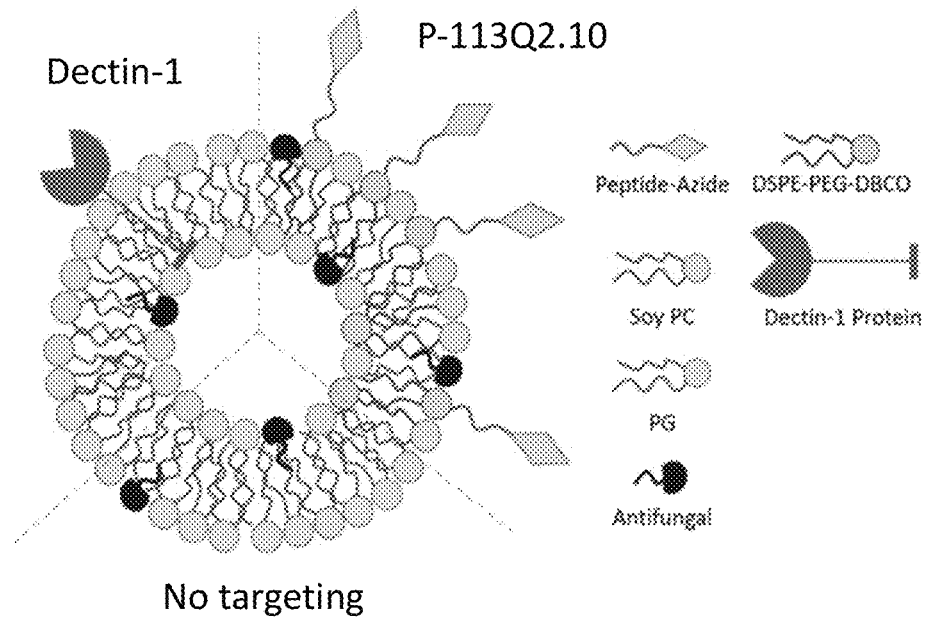
FIG. 1 is a schematic representation of the liposome formulation embodiments.
Figure 2:
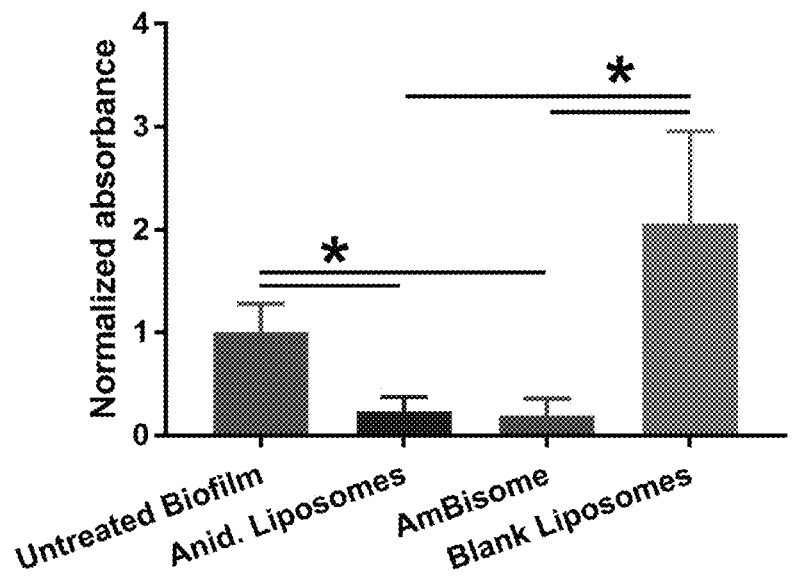
FIG. 2 is a chart showing normalized biofilm remaining after twenty-four hours (*$p<0.05$, n=3, two-tailed unpaired t-test).
Figure 3:
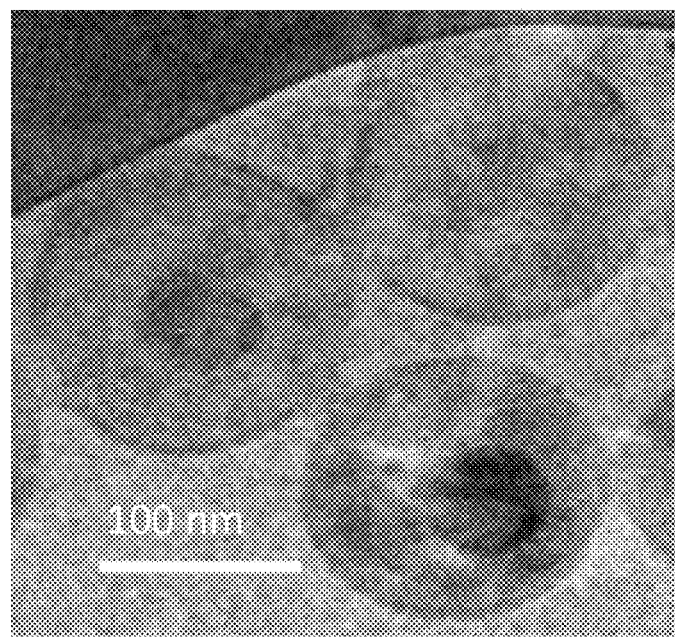
FIG. 3 is a cryo-transmission electron micrograph (cryo-TEM) of dectin-1 liposomes loaded with anidulafungin.

The functionalized liposomal formulations contain antifungals useful for clinicians to treat systemic candidiasis actively. Clinicians can use the functionalized liposomal formulations for delivering an antifungal because they specifically target and attach to *Candida* spp. (including *Candida albicans*, but also including *Candida auris*, *Candida glabrata*, *Candida parapsilosis*, *Candida tropicalis*, and other *Candida* species). Using functionalized liposomal formulations reduces the free drug necessary for an equivalent treatment, which aids in preventing the spread of antimicrobial resistance. Using functionalized liposomal formulations increases the solubility of hydrophobic antifungals (i.e., echinocandins and other classes) and decreases off-site and systemic toxicity of antifungals (reducing unwanted side-effects).

Using functionalized liposomal formulations increases the effect of antifungal molecules. Using functionalized liposomal formulations increases the solubility of these antifungal molecules. Using functionalized liposomal formulations also lengthens the useful lifetime of these antifungal products.

Definitions

"Administer" or "administered" refers to applying, ingesting, inhaling, or injecting, or prescribing an active ingredient (e.g., an antifungal) to treat a host or patient needing treatment. See, US 2016/0199351 A1 (Rappleye et al.) "Compositions and methods for inhibiting fungal infections." Medically-acceptable routes of administration can include the intravenous route, the subcutaneous route, the intraperitoneal route, and the like.

"Anidulafungin" is a semi-synthetic lipopeptide synthesized from a fermentation product of *Aspergillus nidulans*. Anidulafungin is an echinocandin, a class of antifungal drugs that inhibit the synthesis of 1,3-β-D-glucan, an essential component of fungal cell walls. Anidulafungin is 1-[(4R, 5R) 4,5-dihydroxy-N2-[[4"-(pentyloxy)[1,1':4',1"-terphenyl]-4-yl] carbonyl]-L-ornithine] echinocandin B. Anidulafungin is a white to off-white powder practically insoluble in water and slightly soluble in ethanol. The empirical formula of anidulafungin is $C_{58}H_{73}N_7O_{17}$, and the formula weight is 1140.3. See, US 2009/0238867 A1 (Boston Univ., Pacgen Biopharmaceuticals Corp.) "Antifungal formulation and method of preparation." Anidulafungin is not freely soluble in water. See, E.P. 3 058 958 B1 (Selectchemie AG) "Anidulafungin composition."

"Antifungal" is a drug used to prevent fungal growth or is active against fungi. See, New Oxford American Dictionary, online. Examples of antifungals are clotrimazole, econazole, ketoconazole, miconazole, tioconazole, nuconazole, posaconazole, itraconazole, voriconazole, isavuconazonium, terbinafine, nystatin, amorolfine, griseofulvin, caspofungin, micafungin, anidulafungin, tavaborole, miconazole, and amphotericin B deoxycholate. See, US 2016/0199351 A1 (Rappleye et al.) "Compositions and methods for inhibiting fungal infections." "*Candida*" are small thin-walled ovoid yeasts that reproduce by budding. *Candida* organisms appear in three forms in tissues; blastospores, pseudohyphae, and hyphae. The genus *Candida* contains over 150 species, only a few of which cause disease in humans. *Candida* infections can be mucocutaneous or invasive. Invasive candidiasis is an opportunistic infection caused by several *Candida* fungal species, including *C. albicans, C. auris, C. guilliermondii, C. krusei, C. parapsilosis, C. tropicalis, C. lusitaniae, C. dubliniensis*, and *C. glabrata*. *Candida* causes life-threatening infections by invading the bloodstream (candidemia) or by invading deep-seated organs. See, US 2016/0199351 A1 (Rappleye et al.) "Compositions and methods for inhibiting fungal infections."

"Dectin-1" is a transmembrane protein containing an immunoreceptor tyrosine-based activation (ITAM)-like motif in its intracellular tail (which is involved in cellular activation) and one C-type lectin-like domain (carbohydrate-recognition domain, CRD) in the extracellular region (which recognizes β-glucans and endogenous ligands on T cells). The CRD is separated from the membrane by a stalk region. CLEC7A contains putative N-linked sites of glycosylation in the stalk region. Drummond & Brown "The role of Dectin-1 in the host defense against fungal infections". Curr. Opin. Microbiol. 14 (4): 392-9 (2011); Brown et al., "Structure of the fungal beta-glucan-binding immune receptor dectin-1: implications for function". Protein Sci. 16 (6): 1042-52 (2007).

"P-113Q2.10" is a fragment of the antimicrobial Histatin 5 peptide, which is capable of electrostatic interaction with the yeast cell wall before binding to the heat shock protein, SSa1, in the membrane. See, Jang et al., Journal of Antimicrobial Agents and Chemotherapy, 52(2), 497-504 (February 2008).

"Echinocandins" are large lipopeptide molecules that are inhibitors of glucan synthase, which disrupts β-(1,3)-glucan formation as an essential component of the fungal cell wall, destabilizing the integrity of the fungal cell wall, and leading to osmotic instability and cell death. See, WO 2017/037232 A1 (Xellia Pharmaceuticals APS) "Anidulafungin formulations." The first echinocandin to be approved for medical use was caspofungin, followed by micafungin and anidulafungin. Due to the poor absorption after oral administration, using echinocandins is usually limited to the intravenous route. See, E.P. 3 058 958 B1 (Selectchemie AG) "Anidulafungin composition."

"Liposome" or "liposomal formulation" is a minute spherical sac of phospholipid molecules enclosing a water droplet, primarily as formed artificially, to carry drugs or other substances into the tissues. See, New Oxford American Dictionary, online. A liposome vesicle has at least one lipid bilayer.

"Lipopeptide" is a molecule consisting of a lipid connected to a peptide. Hamley, "Lipopeptides: from self-assembly to bioactivity." Chemical Communications (Cambridge, England). 51 (41): 8574-83 (May 2015).

"Pharmaceutically acceptable" means that the formulation does not cause an unacceptable loss of antifungal activity or intolerable adverse side effects.

"Therapeutically effective amount" of the anidulafungin compound is an amount of antifungal administered to a patient sufficient to produce a therapeutic response to one or more symptoms of the disease being treated.

"Unilamellar" liposome is a spherical chamber/vesicle, bounded by a single bilayer of an amphiphilic lipid or a mixture of such lipids, containing aqueous solution inside the chamber. Unilamellar liposomes mimic cell membranes and are classified based upon their size.

A Liposomal Formulation Comprising an Antifungal

The inventors have successfully incorporated a lipopeptide echinocandin, anidulafungin, into unilamellar liposomes. Anidulafungin shows low minimum inhibitory concentrations (MICs) against *Candida* spp. (0.25 µg/mL for *Candida albicans* to 4 µg/mL for *Candida parapsilosis*). Anidulafungin exhibits reduced toxicity to human cells compared to many other antifungals. Vazquez & Sobel, Clinical Infectious Diseases, 43(2), 215-222 (2006). However, the drug is highly hydrophobic, making drug solubilization and administration a formidable challenge. The inventors have overcome this challenge by the liposomal incorporation of anidulafungin. This technology can be adapted to incorporate other antifungals into liposomes.

For methods of incorporating antifungals into liposomes, see U.S. Pat. No. 9,539,273 (Meehan et al.) "Targeted delivery of antifungal agents" and AU 57355/00 A (Liposome Co Inc) "Peptide-lipid conjugates, liposomes, and liposomal drug delivery" (also published as WO 2001/000247 A9).

Using a freeze-thaw and extrusion method, the inventors made liposomes containing the lipids, hydrogenated soy phosphatidylcholine, cholesterol, phosphatidylglycerol, α-tocopherol, and anidulafungin at 60.73%, 14.83%, 23.95%, 0.18%, and 0.31% w/w respectively (designated the 1× formulation). Dynamic light scattering (DLS) of the 1× formulation showed an average liposome diameter of 99.27±1.16 nm and a polydispersity index of 0.07±0.03. The inventors also developed two additional formulations. One was the 5× formulation (containing the lipids, hydrogenated soy phosphatidylcholine, cholesterol, phosphatidylglycerol, α-tocopherol, and anidulafungin at 59.98%, 14.65%, 23.66%, 0.18%, and 1.53% w/w, respectively). The other was the 10× formulation (containing the lipids, hydrogenated soy phosphatidylcholine, cholesterol, phosphatidylglycerol, α-tocopherol, and anidulafungin at 59.08%, 14.43%, 23.30%, 0.17%, and 3.02% w/w, respectively). Additional formulations with varying concentrations can be developed.

The inventors also incorporated targeting moieties, including dectin-1, a transmembrane protein that binds to fungal cell wall glucan. Dectin-1 is included during the dry lipid film hydration.

The inventors also incorporated other targeting moieties, including P-113Q2.10 (SEQ ID NO: 2), a fragment of the antimicrobial peptide, histatin 5, which interacts electrostatically with the fungal cell wall before binding to heat shock protein SSa1. Jiang et al., Journal of Controlled Release, 279, 316-325 (2018) first described the incorporation of P-113 peptide fragment (SEQ ID NO: 1) into the liposomes. To incorporate P-113Q2.10 (SEQ ID NO: 2) into liposomes, the inventors decorated liposomes with poly(ethylene glycol) (PEG) by incorporating lipids (phosphoethanolamine) functionalized with PEG into the vesicle composition. The PEG, functionalized with dibenzocyclooctyne (DBCO), can then be covalently attached to azide-functionalized P-113Q2.10 (SEQ ID NO: 2) using strain promoted click chemistry.

The inventors incorporated fluorescent phosphoethanolamine-lissamine rhodamine B into liposomal targeting formulation. The localization to fungal cells was evident with the palmitic acid-P113Q2.10 liposome after twenty-four hours. See, EXAMPLE 5 below.

The inventors incorporated calcofluor white into liposomes at 1.5% w/w. Calcofluor white encapsulation was calculated to be 34% and 78% for liposomes with and without the antifungal anidulafungin. Both calcofluor white liposome formulations bound to fungal cells. The fungal burden decreased when incubated with calcofluor white liposomes as compared to fungal cells in media only, suggesting antifungal activity. See, EXAMPLE 6 below.

A Method for Treating *Candida* Infections

This formulation containing the antifungal, anidulafungin, has shown promise as a therapeutic against planktonic and biofilm *Candida*, the most common cause of fungal infections.

Drug-loaded liposomes were tested against *Candida albicans* in a microdilution assay. The minimum inhibitory concentration (MIC90) range of these liposomes was 1.5 to 12.5 µg/mL.

Figure 4:
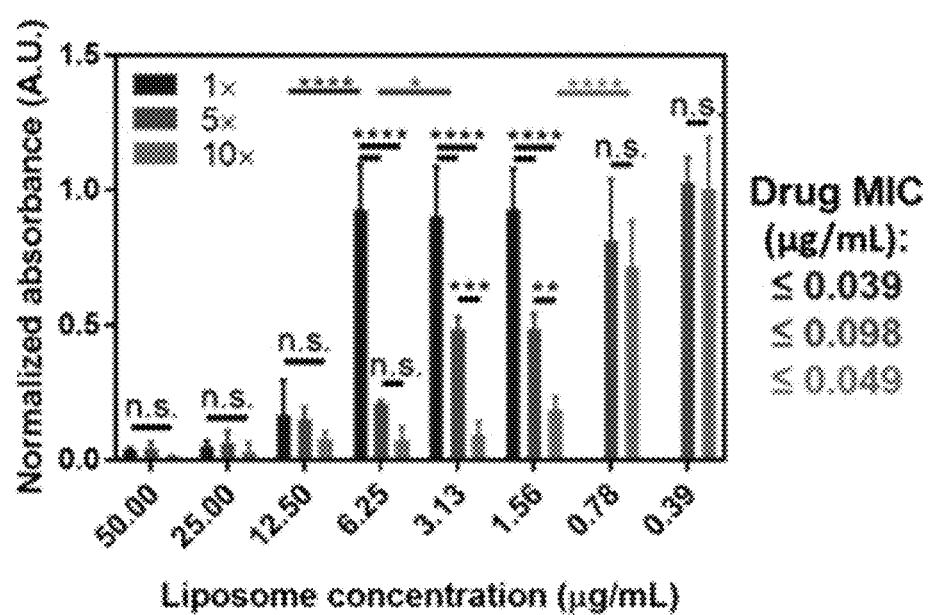
FIG. 4 is a graph showing the in vitro antifungal activity of anidulafungin liposomes incubated with *Candida albicans* versus liposome concentration. The liposome minimum inhibitory concentrations (MIC) and corresponding drug MIC (based on theoretical loading) are indicated. The graph shows data for three different drug loading concentrations (1×, 5×, and 10×).
Figure 5:
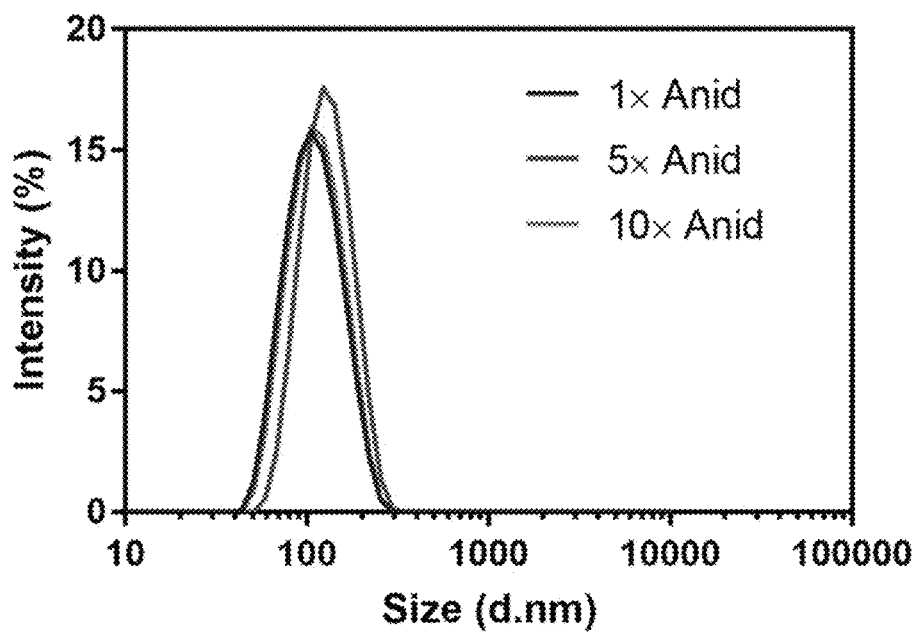
FIG. 5 is a dynamic light scattering spectra of three different liposome formulations (1×, 5×, and 10× drug loading).

The drug-loaded liposomes were determined to have a minimum inhibitory concentration (MIC) against *Candida albicans* (ATCC 10231) of 1.5 to 12.5 µg/mL (corresponding to 0.04 to 0.1 µg/mL anidulafungin) as shown in FIG. 4.

The inventors compared anidulafungin-loaded liposomes with AmBisome®, a commercially-available liposomal amphotericin B, for activity against *Candida albicans* 10231 biofilms. AmBisome® localizes to the fungal cell wall. See, Adler-Moore & Proffitt, Journal of Antimicrobial Chemotherapy, 49(1), 21-30 (2002) and Walker et al., mBio, 9(1), e02383-17 (2018). The anidulafungin-loaded liposomes performed as AmBisome®, reducing fungal burden by five-fold after only twenty-four hours. See, FIG. 4.

Figure 6:
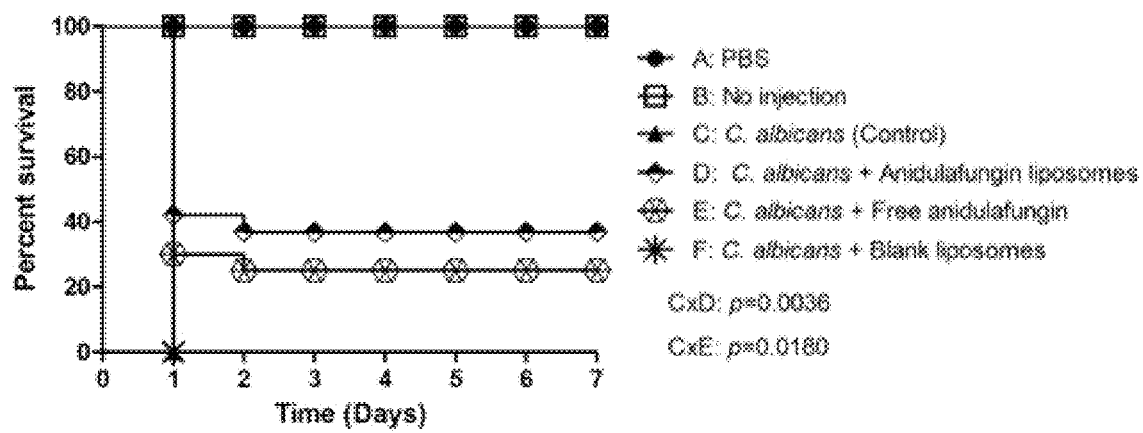
FIG. 6 is a graph showing the survival of *Candida albicans* SC5314 infected *Galleria mellonella* larvae treated with 1× liposomes and free anidulafungin. These results demonstrate that the 1× formulation tested is effective at increasing *G. mellonella* survival for at least seven days.

FIG. 6 shows the survival of *Candida albicans* SC5314 infected *Galleria mellonella* larvae treated with 1× liposomes and free anidulafungin. These results demonstrate that the 1× formulation tested is effective at increasing *Galleria mellonella* survival for at least seven days.

The following Examples are provided to illustrate the invention and should not be considered to limit its scope in any way.

Example 1

Fabricating Additional Antifungal Nanoparticle Formulations to Confirm In Vitro Activity Motivated by the success of the anidulafungin-incorporating liposomes, this Example examines the fabrication of other nanoparticle formulations using the same lipid composition but incorporating different antifungal drugs. To complete the in vivo characterization of the liposomal therapeutics that the inventors have developed and characterized, including the anidulafungin liposome formulations but also including formulations of other antifungal liposomes based upon this work, the inventors are generating a library of antifungal nanoparticles. The inventors are investigating the in vitro and in vivo efficacy of these additional formulations, providing the data to enable clinical translation. The inventors are also examining the stability and scale-up of these liposomal formulations to enhance treatment options for fungal infections.

The efficacy of a library of antifungal encapsulating liposomal nanoparticles will be tested in vitro and in vivo. After the identification of a lead nanoparticle, the lead particle will be scaled up and tested for stability.

Antifungal drugs, including echinocandin B, cilofungin, micafungin, and caspofungin, are of interest. (Other drugs of interest include other classes such as polyenes and azoles.) Anidulafungin, micafungin, and caspofungin are clinically approved, but solubility remains a challenge during administration. Although having shown promise against *Candida* spp., cilofungin was removed from clinical trials due to toxicity. Odds et al., Trends in Microbiology, 11(6), 272-279 (2003). Echinocandin B is not used clinically due to associated hemolysis. Hashimoto, "Micafungin: a sulfated echinocandin." J. Antibiotics, 62(1), 27 (2009); Barrett, "From natural products to clinically useful antifungals." Biochimica et Biophysica Acta-Molecular Basis of Disease, 1587(2-3), 224-233 (2002). Incorporating these antifungals into liposomes can increase solubility, decrease toxicity, and render these antifungals clinically viable, thus, increasing the arsenal of therapeutics available to treat life-threatening fungal infections. Dynamic light scattering (DLS) and cryo-transmission electron microscopy (cryo-TEM) will confirm liposome formulation. In vitro efficacy of the formulations against *Candida albicans, Candida glabrata, Candida parapsilosis, Candida tropicalis*, or another *Candida* species can be examined in microdilution and biofilm assays. Mammalian cell viability comparing liposomal formulations with the free drug can also be investigated.

Example 2

Nanoparticle Activity and Toxicity In Vivo in Systemic Fungal Infections

The objective of this Example is to determine the efficacy of the liposomal antifungal formulations in reducing systemic *Candida* burden and off-site toxicity compared to free drug in *Galleria mellonella* (wax moth) larvae and murine infection models, which have been widely used to study the pathogenic mechanisms of *Candida albicans*.

Initially, the liposome library can be tested in *Galleria mellonella* larvae, which are used in infection models due to their cellular and humoral innate immune response, which correlates with mammalian responses to virulence. See, Jiang et al., J. Controlled Release, 279, 316-325 (2018); Tsai et al., Virulence, 7(3), 214-229 (2016). Healthy larvae of similar size are injected in the last left proleg using a 29-gauge needle with five µL of wild-type *Candida albicans* (5×10^5 CFU) in sterile saline. This concentration kills *Galleria mellonella* larvae within 100 hours. See, Li et al., Biological and Pharmaceutical Bulletin, 36(9), 1482-1487 (2013). The free antifungal drug, liposomal formulations, with and without loaded antifungal, and saline controls are injected similarly in the last right proleg. Concentrations injected range ±25% from the clinically used dose for the antifungal drug. Liposomal treatments deliver the equivalent antifungal dose as free drug groups.

The larvae are incubated at 37° C. The number of dead larvae is scored daily. Controls of non-*Candida* infected *Galleria mellonella* are included to control for the effect of needle-induced trauma.

FIG. 6 shows the survival of *Candida albicans* SC5314 infected *Galleria mellonella* larvae treated with 1× liposomes and free anidulafungin. These results demonstrate that the 1× formulation tested is effective at increasing *G. mellonella* survival for at least seven days.

Liposomal formulations that improve survival over free drug are then examined in a murine systemic *Candida* infection model. BALB/c mice will be infected with 100 µL of *Candida albicans* (5×10^5 CFU) in sterile saline by the tail vein using a 27-gauge needle. After two hours, the treatments will be injected intraperitoneally at different dosages (free drug, liposomes with and without loaded antifungal, and saline). Mice are monitored daily, and their survival quantified. *Candida glabrata, Candida parapsilosis, Candida tropicalis*, and other *Candida* strains will be tested with the most potent liposomal formulations.

Example 3

Nanoparticle Scale-Up and Storage Stability

Liposome fabrication occurs in aqueous conditions. Liposomes or encapsulated therapeutics can disrupt over time. To store these liposomes or encapsulated therapeutics for extended periods (i.e., years), those having ordinary skill in the liposome formulation art should use methods of drying the formulations that do not compromise vesicle structure. Different cryoprotectants and lyoprotectants should be used as additives to protect the liposomes during freeze-drying and prolonged storage.

Scaling liposome production is important for a successful clinical translation. Those having ordinary skill in the liposome formulation art can use established expertise in pharmaceutical and liposomal storage and scale-up, to enable robust characterization of the antifungal formulations developed (i.e., anidulafungin liposomes) for translation and fabrication of additional formulations.

Example 4

Fabrication with Anidulafungin

Figure 7:
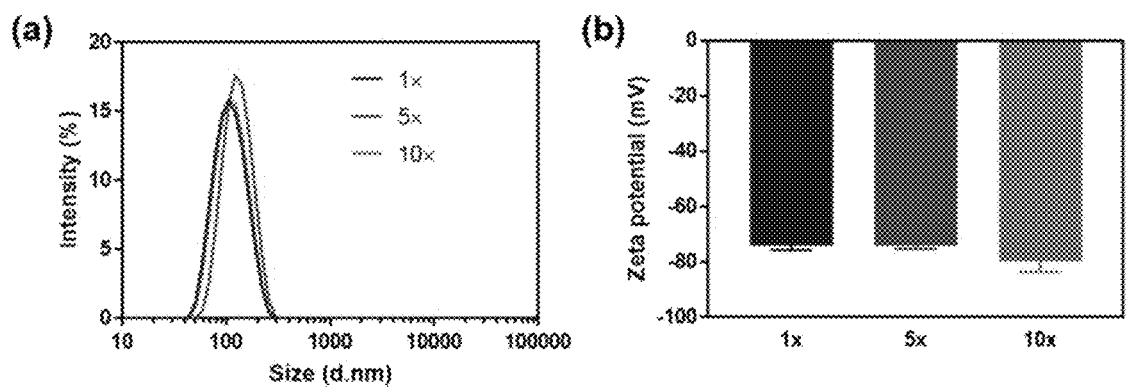
FIG. 7 is a pair of graphs showing the characterization of 1×, 5×, and 10× anidulafungin loaded liposomes. (a) A pair of bell curves showing the liposome hydrodynamic diameter distribution as determined by dynamic light scattering. (b) A bar graph showing the potential of anidulafungin loaded liposomes in water ($p>0.05$, not significant; one-way ANOVA with Tukey's post-hoc analysis, n=3).
Figure 8:
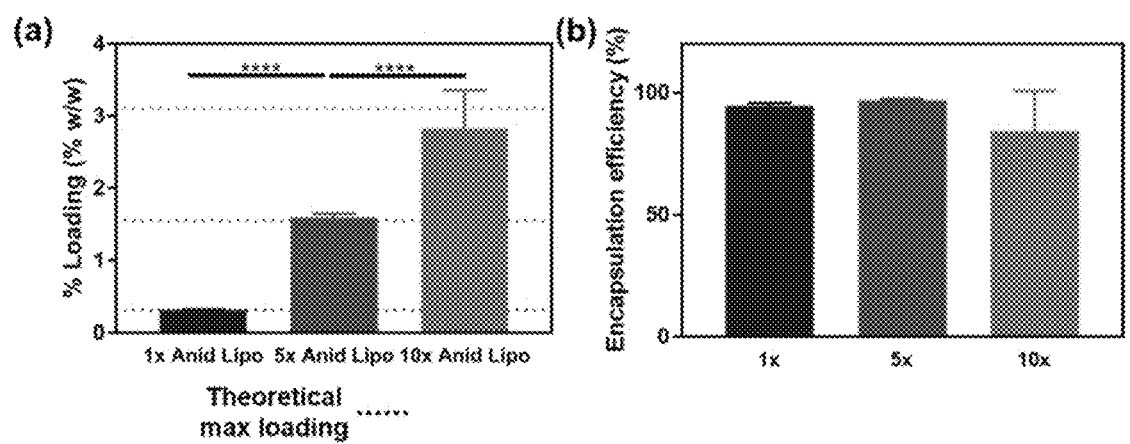
FIG. 8 is a pair of bar graphs that show the successful encapsulation of anidulafungin in 1×, 5×, and 10× liposomes. (a) Anidulafungin liposome drug loading (****$p<0.0001$, one-way ANOVA with Tukey's post-hoc analysis, n=6). (b) Anidulafungin liposome encapsulation efficiency ($p>0.05$, not significant; one-way ANOVA with Tukey's post-hoc analysis, n=6).

The inventors fabricated ~100 nm particles (see FIG. 7(c)) with negative potential (see FIG. 7(b)) encapsulating the antifungal drug anidulafungin. The inventors loaded anidulafungin at three different concentrations based on the liposome mass: 0.31% w/w (1×), 1.55% w/w (5×), 3.10% (10×), achieving drug loading comparable to the theoretical values (see, FIG. 8a) and high encapsulation efficiencies (see FIG. 8(b)).

The 1× anidulafungin liposomes showed remarkable stability in solution at 4° C. for up to 140 days. The inventors observed no significant changes in vesicle size (see, FIG. 9a). Although minimal amounts of encapsulated drug were lost (see, FIG. 7(b)), the liposomes were just as effective as freshly prepared liposomes in inhibiting *Candida albicans* 10231 growth (see, FIG. 9(c)).

Figure 9:
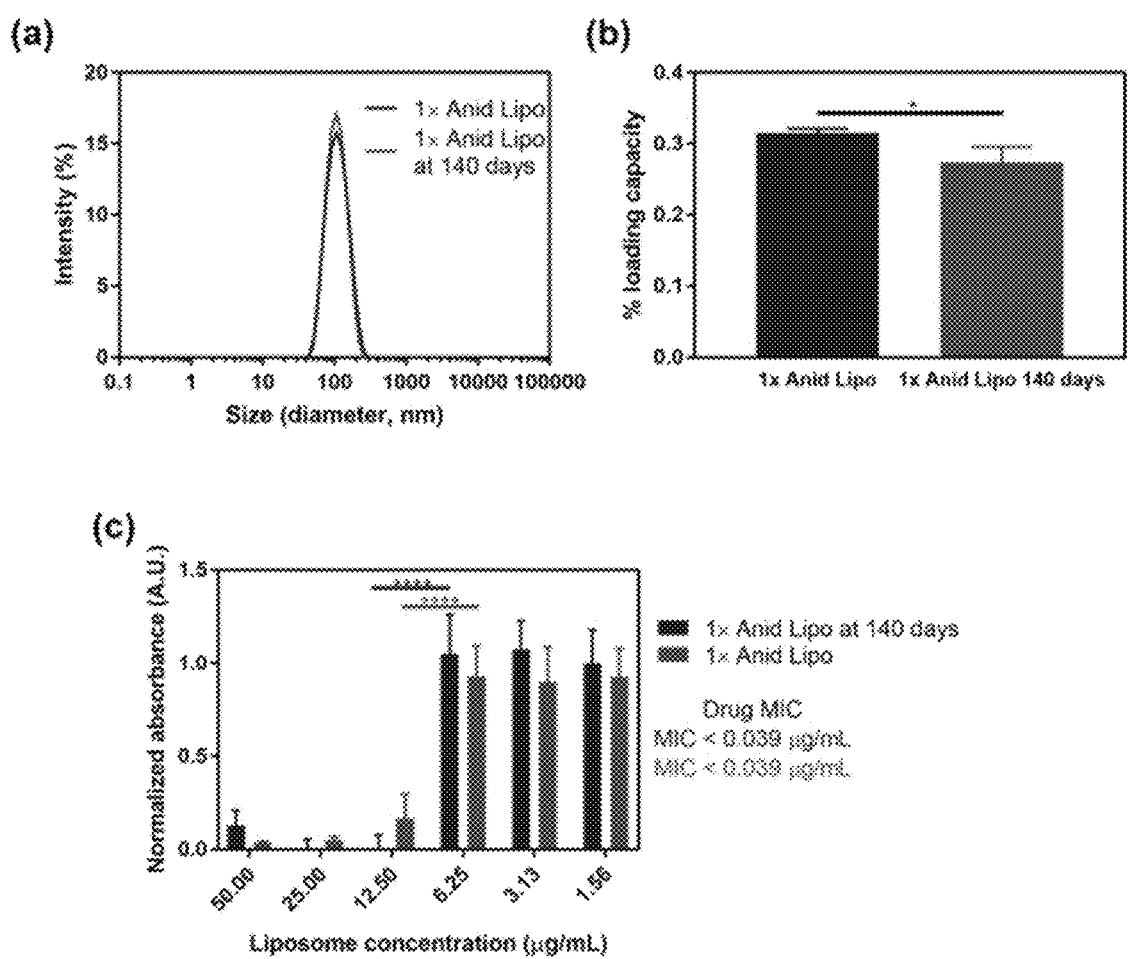
FIG. 9 is a set of graphs showing the stability of 1× anidulafungin liposomes after 140 days of aqueous storage at 4° C. (a) A pair of bell curves showing the liposome hydrodynamic diameter distribution of freshly made 1× anidulafungin liposomes compared to 1× anidulafungin liposomes stored at 4° C. in water for 140 days determined by dynamic light scattering. (b) A bar graph showing the drug loading of freshly made 1× anidulafungin liposomes compared to 1× anidulafungin liposomes stored at 4° C. in water for 140 days (*p<0.05, unpaired two-tailed t-test, n=3). (c) A bar graph showing the results of a microdilution assay of freshly made 1× and 1× anidulafungin loaded liposomes stored at 4° C. in water for 140 days against *Candida albicans* 10231 (****p<0.0001, two-way ANOVA with Tukey's post-hoc analysis, n=3).
Figure 10:
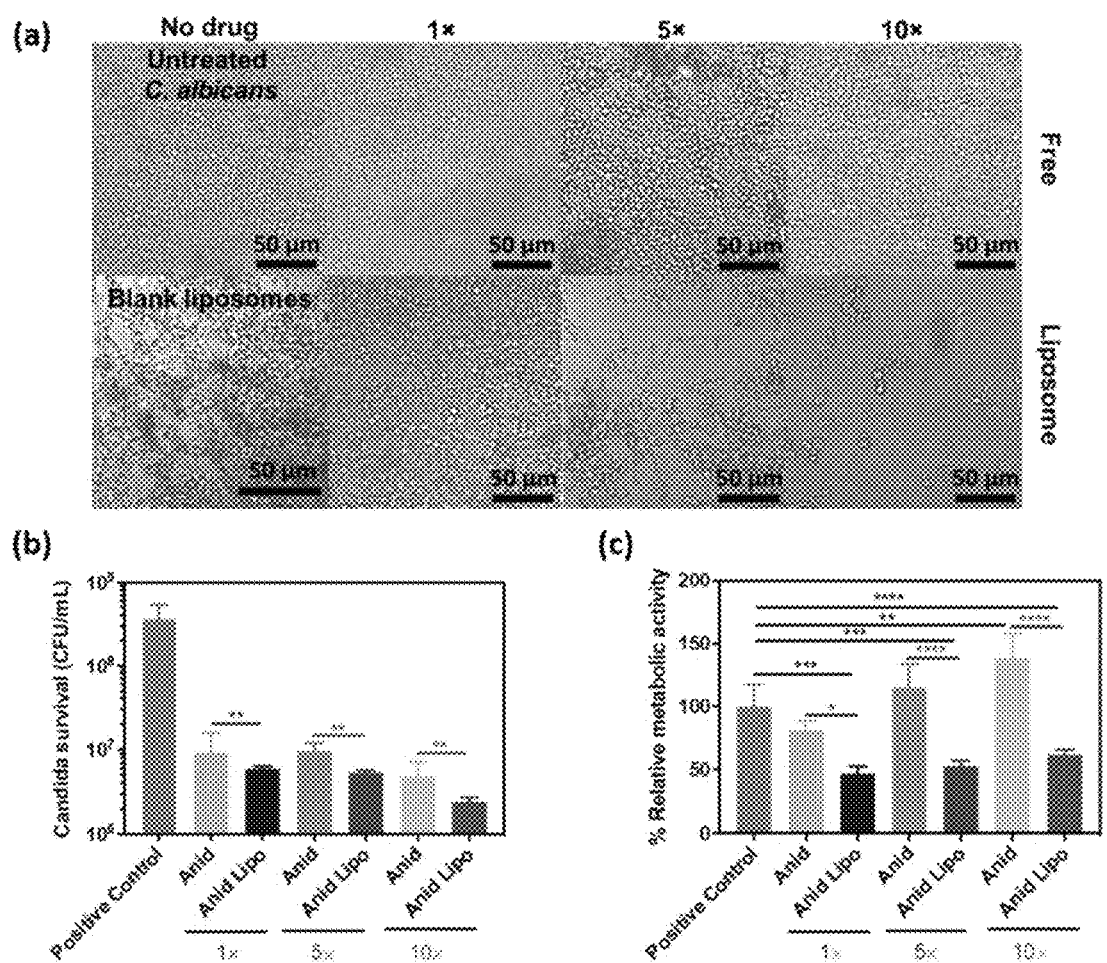
FIG. 10 shows that nidulafungin liposomes demonstrate increased activity against mature *Candida albicans* biofilms compared to free drug. (a) A set of representative differential interference contrast microscopy images of *Candida albicans* 10231 biofilms after twenty-four hours of treatment with 1×, 5×, and 10× anidulafungin loaded liposomes or equivalent free drug. (b) A bar graph showing *Candida albicans* 10231 biofilm colony-forming units (CFU) twenty-four hours after treatment with 1×, 5×, and 10× anidulafungin loaded liposomes or equivalent free drug (**p<0.01, unpaired two-tailed t-test, n=4). (c) A bar graph showing relative metabolic activity of *Candida albicans* 10231 biofilm cells twenty-four hours after treatment with 1×, 5×, and 10× anidulafungin loaded liposomes or equivalent free drug (*p<0.05, p<0.01, *p<0.001, ****p<0.0001, one-way ANOVA with Tukey's post hoc analysis, n=4). Positive controls of untreated cells are shown. Negative controls lacking fungi were included in each study.

Anidulafungin liposomes were more effective than free drug against *Candida* biofilms, which are significantly harder to treat than planktonic fungi. 1×, 5×, and 10× anidulafungin liposomes at 1.25 mg/mL were effective at disrupting pre-formed *Candida albicans* 10231 biofilms after twenty-four hours (see, FIG. 9(*a*)). The inventors observed a two-log reduction in fungal burden when compared to untreated biofilms (see, FIG. 9(*b*)). Additionally, metabolic activity was reduced to approximately 46% compared to untreated controls. Biofilms treated with equivalent concentrations of free anidulafungin did not reduce metabolic activity (see, FIG. 9(*c*)). This result highlights the importance of liposomal carriers in increasing the efficacy of antifungals against biofilms.

Example 5

Fabrication with PEG-P113Q2.10 or Palmitic Acid-P113Q2.10

The inventors evaluated fungal cell localization of PEG-P113Q2.10 and palmitic acid-P113Q2.10 functionalized liposomes using flow cytometry and confocal microscopy. The inventors performed confocal microscopy using fluorescently labeled liposomes. PEG-P113Q2.10 liposomes show little localization and more aggregation, while palmitic acid-P113Q2.10 liposomes show localization to *Candida albicans* SC5314 after twenty-four hours incubation.

Figure 11:
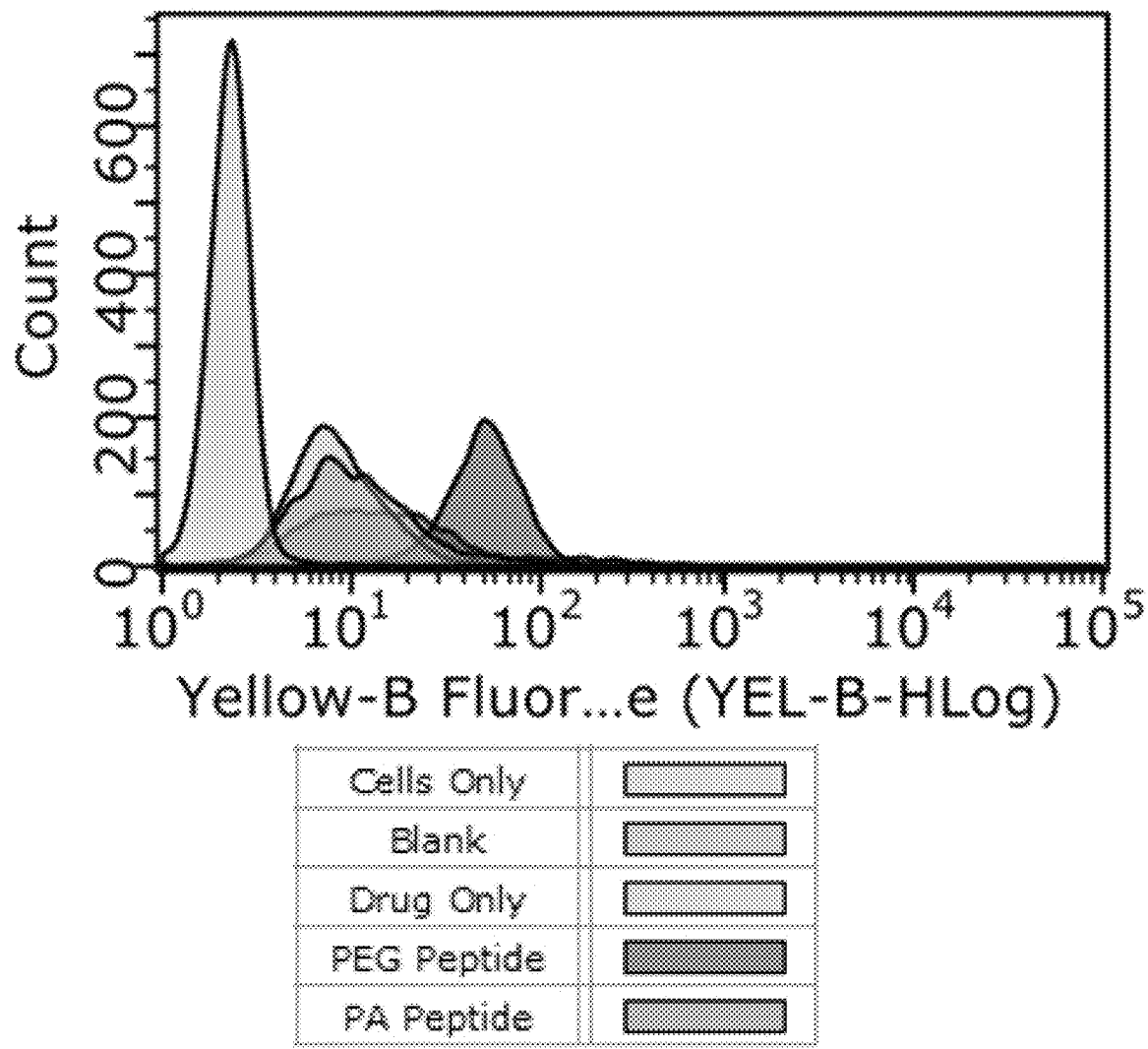
FIG. 11 is a set of bell curves showing the results of flow cytometry with fluorescently labeled liposomes. PEG-P113Q2.10 liposomes show higher interaction with *Candida albicans* SC5314 cells.

Fluorescent phosphoethanolamine-lissamine rhodamine B was incorporated into each liposomal targeting formulation. PEG-P113Q2.10 liposomes interacted more with *Candida albicans* SC5314 cells compared to palmitic acid-P113Q2.10, non-targeting, and blank liposomes after three hours of incubation (see, FIG. 11). The localization to fungal cells was more evident with the palmitic acid-P113Q2.10 liposome after twenty-four hours.

Example 6

Fabrication with Calcofluor White

The inventors fabricated non-peptide-based targeting liposomes using calcofluor white (CFW), which binds to chitin in the fungal cell wall. The inventors performed confocal microscopy using calcofluor white liposomes, including (a) blank calcofluor white liposomes; (b) anidulafungin calcofluor white liposomes; (c) fungal burden after incubation in media only; (d) fungal burden after incubation with blank calcofluor white liposomes; and (e) fungal burden after incubation with anidulafungin calcofluor white liposomes.

Calcofluor white was incorporated into liposomes at 1.5% w/w. Calcofluor white encapsulation was calculated to be 34% and 78% for liposomes with and without the antifungal anidulafungin. Both calcofluor white liposome formulations could bind to fungal cells. The fungal burden was visually decreased when incubated with calcofluor white liposomes compared to fungal cells in media only, suggesting antifungal activity.

Other Embodiments

Specific compositions and methods have been described. The detailed description in this specification is illustrative and not restrictive. The detailed description in this specification is not intended to be exhaustive or to limit the disclosure to the precise form disclosed. Other equivalents and modifications besides those already described are possible without departing from the inventive concepts described in this specification, as those having ordinary skill in the liposome formulation art recognize. While method steps or functions are presented in a given order, alternative embodiments may perform functions in a different order, or functions may be performed substantially concurrently. Due to biological functional equivalency considerations, some changes can be made in the protein structure without affecting the biological or chemical action in kind or amount. The inventive subject matter is not to be restricted except in the spirit of the disclosure.

When interpreting the disclosure, all terms should be interpreted in the broadest possible manner consistent with the context. Unless otherwise defined, all technical and scientific terms used in this specification have the same meaning as commonly understood by those having ordinary skill in the art to which this invention belongs. This invention is not limited to the particular methodology, protocols, or reagents described in this specification and can vary in practice. The terminology used in this specification is not intended to limit the scope of the invention, which is defined solely by the claims.

All patents and publications cited throughout this specification are expressly incorporated by reference to disclose and describe the materials and methods described in such publications that might be used with the technologies described in this specification. The publications discussed are provided solely for their disclosure before the filing date. They should not be construed as an admission that the inventors are not entitled to antedate such disclosure by prior invention or for any other reason. If there is an apparent discrepancy between a previous patent or publication and the description provided in this specification, the present specification (including any definitions) and claims shall control. All statements as to the date or representation as to the contents of these documents are based on the information available to the applicants and constitute no admission as to the correctness of the dates or contents of these documents. The dates of publication provided in this specification may differ from the actual publication dates. If there is an apparent discrepancy between a publication date provided in this specification and the actual publication date provided by the publisher, the actual publication date shall control.

The terms "comprises" and "comprising" should be interpreted as referring to elements, components, or steps in a non-exclusive manner, indicating that the referenced elements, components, or steps may be present, used, or combined with other elements, components, or steps. The singular terms "a," "an," and "the" include plural referents unless context clearly indicates otherwise. Similarly, the word "or" is intended to include "and" unless the context clearly indicates otherwise. The abbreviation "e.g." is used to indicate a non-limiting example and is synonymous with the term "for example."

When a range of values is provided, each intervening value, to the tenth of the unit of the lower limit, unless the context dictates otherwise, between the upper and lower limit of that range and any other stated or intervening value in that range of values.

Some embodiments of the technology described can be defined according to the following numbered paragraphs:

A composition comprising a liposomal formulation and an antifungal.

The composition, wherein the liposomal formulation is a unilamellar liposomal formulation.

The composition, wherein the antifungal is selected from the group consisting of antifungal lipopeptides, azoles, polyenes, allylamines, and nucleosides.

The composition, wherein the antifungal is an antifungal echinocandin.

The composition, wherein the antifungal is selected from the group consisting of anidulafungin, echinocandin B, cilofungin, micafungin, and caspofungin.

The composition, further comprising a P-113Q2.10-PEG lipid decoration.

The composition, further comprising dectin-1.

The composition, further comprising a P-113Q2.10-PEG lipid decoration or a palmitic acid decoration.

A method of making a liposomal formulation, comprising the steps of a freeze-thaw, sonication, and extrusion method, wherein the liposomal formulation comprises the lipids hydrogenated soy phosphatidylcholine, cholesterol, phosphatidylglycerol, and α-tocopherol, and an antifungal selected from the group consisting of, but not limited to, anidulafungin, echinocandin B, cilofungin, micafungin, and caspofungin.

The method, wherein the Candida infection is candidiasis, and wherein the administering step comprises administering the liposomal formulation to a subject who has candidiasis.

The method, wherein the Candida infection is systemic candidiasis, and wherein the administering step comprises administering the liposomal formulation to a subject who has systemic candidiasis.

The method, wherein the Candida infection is a Candida biofilm, and wherein the administering step comprises administering the liposomal formulation to a subject who has a Candida biofilm.

The method, wherein the liposomal formulation has a minimum inhibitory concentration range of 1.5 to 12.5 µg/mL.

The method, where the treatment reduces fungal burden by five-fold after only twenty-four hours.

```
                       SEQUENCE LISTING

<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Lys Arg His His Gly Tyr Lys Arg Lys Phe His
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Gln Arg His His Gly Tyr Lys Arg Gln Phe His
1               5                   10
```

The method, wherein the liposomal formulation comprises the lipids hydrogenated soy phosphatidylcholine, cholesterol, phosphatidylglycerol, and α-tocopherol, and the antifungal at a mass concentration (% w/w) of 60.73%, 14.83%, 23.95%, 0.18%, and 0.31% respectively.

The method, wherein the liposomal formulation comprises of any lipid or lipid-like structure, natural or synthetic, or any amphiphilic molecule or combination of, and an antifungal, decorated with P-113Q2.10 and dectin-1 targeting moieties.

The method, wherein the liposomes have an average diameter of 100 to 1000 nm (polydispersity index (PDI)=0 to 0.5).

The method, further comprising the steps of measuring vesicle size and PDI using dynamic light scattering (DLS).

A method for treating a Candida infection, comprising the step of administering a liposomal formulation comprising an antifungal lipopeptide to a subject with a Candida infection.

The method, wherein the Candida infection is a bloodstream Candida infection, and wherein the administering step comprises administering the liposomal formulation to a subject who has a bloodstream Candida infection.

We claim:

1. A composition comprising a Candida-targeted unilamellar liposomal formulation and an antifungal, wherein the antifungal is selected from the group of echinocandins consisting of anidulafungin, echinocandin B. cilofungin, micafungin, and caspofungin, with the proviso that the antifungal is not the polyene, amphotericin B, wherein the unilamellar liposomal formulation further comprises either a palmitic acid, wherein the palmitic acid is covalently linked to P-113Q2.10, such that the unilamellar liposomal formulation comprises the P-113Q2.10 peptide decoration as a fungi targeting moiety, a P-113Q2.10-poly(ethylene glycol) (PEG) or poly(ethylene glycol) (PEG) conjugated to a lipid, wherein the PEG is covalently linked to P-113Q2.10, such that the unilamellar liposomal formulation comprises the P-113Q2.10 peptide decoration as a targeting moiety.

2. A composition comprising a Candida-targeted unilamellar liposomal formulation and an antifungal, wherein the antifungal is selected from the group of echinocandins consisting of anidulafungin, echinocandin B. cilofungin, micafungin and caspofungin, in with the proviso that the antifungal is not the polyene, amphotericin B, wherein the unilamellar liposomal formulation further comprises a palmitic acid, wherein the palmitic acid is covalently linked to a P-113Q2.10-PEG and the composition further comprises dectin-1.

* * * * *